United States Patent [19]
Bogaty et al.

[11] Patent Number: 5,440,210
[45] Date of Patent: Aug. 8, 1995

[54] INDIRECTLY SENSING ACCELERATOR BEAM CURRENTS FOR LIMITING MAXIMUM BEAM CURRENT MAGNITUDE

[75] Inventors: John M. Bogaty, Lombard; Benny E. Clifft, Park Forest; Lowell M. Bollinger, Downers Grove, all of Ill.

[73] Assignee: University of Chicago, Chicago, Ill.

[21] Appl. No.: 48,652

[22] Filed: Apr. 16, 1993

[51] Int. Cl.$^6$ .............................. H01J 29/52
[52] U.S. Cl. ............................ 315/383; 348/380
[58] Field of Search .................... 348/380–382; 315/383–386, 371, 501, 507; 328/233

[56] References Cited

U.S. PATENT DOCUMENTS

| | | | |
|---|---|---|---|
| 3,165,629 | 1/1965 | Okabe | 250/49.5 |
| 3,179,804 | 4/1965 | Gibney et al. | 250/83.3 |
| 3,383,590 | 5/1968 | Koontz et al. | 325/58.5 |
| 3,674,932 | 7/1972 | Griepentrog | 348/380 |
| 3,691,377 | 9/1972 | Matsui et al. | 250/49.5 |
| 3,784,909 | 1/1974 | Schutt et al. | 324/71 |
| 3,838,284 | 9/1974 | McIntyre et al. | 250/385 |
| 3,882,314 | 5/1975 | Benedetti et al. | 250/505 |
| 3,924,067 | 12/1975 | Arneson | 348/380 |
| 4,045,742 | 8/1977 | Meehan et al. | 315/383 |
| 4,058,730 | 11/1977 | Meyer et al. | 250/397 |
| 4,126,884 | 11/1978 | Shanley, II | 348/380 |
| 4,137,552 | 1/1979 | Serafini | 348/380 |
| 4,487,737 | 12/1984 | Bridges | 379/119 |
| 5,177,413 | 1/1993 | Wilber | 315/383 |

*Primary Examiner*—Stephen Brinich
*Attorney, Agent, or Firm*—Reinhart, Boerner, Van Deuren, Norris & Rieselbach

[57] ABSTRACT

A beam current limiter for sensing and limiting the beam current in a particle accelerator, such as a cyclotron or linear accelerator, used in scientific research and medical treatment. A pair of independently operable capacitive electrodes sense the passage of charged particle bunches to develop an RF signal indicative of the beam current magnitude produced at the output of a bunched beam accelerator. The RF signal produced by each sensing electrode is converted to a variable DC voltage indicative of the beam current magnitude. The variable DC voltages thus developed are compared to each other to verify proper system function and are further compared to known references to detect beam currents in excess of pre-established limits. In the event of a system malfunction, or if the detected beam current exceeds pre-established limits, the beam current limiter automatically inhibits further accelerator operation. A high Q tank circuit associated with each sensing electrode provides a narrow system bandwidth to reduce noise and enhance dynamic range. System linearity is provided by injecting, into each sensing electrode, an RF signal that is offset from the bunching frequency by a pre-determined beat frequency to ensure that subsequent rectifying diodes operate in a linear response region. The system thus provides a large dynamic range in combination with good linearity.

18 Claims, 4 Drawing Sheets

TWENTY FIVE PERCENT MODULATION

INDIRECTLY SENSING ACCELERATOR BEAM CURRENTS FOR LIMITING MAXIMUM BEAM CURRENT MAGNITUDE

CONTRACTUAL ORIGIN OF THE INVENTION

The United States Government has rights in this invention pursuant to Contract No. W-31-109-ENG-38 between the U.S. Department of Energy and The University of Chicago, representing Argonne National Laboratory.

BACKGROUND OF THE INVENTION

This invention relates generally to current limiters and, more particularly, to limiters for limiting beam current in a high energy particle accelerator such as a cyclotron or linear accelerator.

High energy particle accelerators, such as cyclotrons and linear accelerators, are widely used in research laboratories and health care facilities. Because of the high energies involved and the consequent possibility of developing potentially harmful radiation, human safety requires that precautions be taken against conditions that could accidentally generate excessive or harmful radiation.

One potentially harmful condition results when the number of charged particles being accelerated (i.e., the beam current) unintentionally exceeds a pre-established upper limit. Through operator error or equipment malfunction, the actual beam current can exceed that which is desired. Such a condition is especially possible when a particular application requires that the accelerator be operated at less than its maximum capacity. In a medical treatment setting, such an overcurrent condition could result in an excessive dose of radiation being delivered to a patient. In a scientific research setting, such a condition could expose the research facility personnel to potentially harmful radiation.

In the past, excess radiation conditions have been avoided by placing radiation detectors at various locations in the accelerator facility. The detectors themselves were selected on the basis of the type, direction and field strength of the radiation anticipated. A computer-based system received information from the sensors and automatically shut down the accelerator in the event excessive radiation was sensed by one or more of the detectors. Although effective in avoiding prolonged exposure to excessive radiation, the system nevertheless had some deficiencies. Frequently, as much as one second was required for the system to detect excessive radiation and shut down the accelerator. A significant radiation overdose could be received by the operating personnel during that time. Furthermore, the effectiveness of the system depended on the proper selection and positioning of the radiation detectors. Thus, it was possible that some excess beam current events were never detected because they did not cause excessive radiation at the locations of the radiation detectors. Such events could, however, cause undetected excessive radiation where the radiation detectors were not located. Any personnel in such locations could unknowingly be exposed to excessive radiation.

In view of the foregoing, a need exists for a particle accelerator beam current limiter that directly senses the beam current with accuracy and reliability and that automatically terminates excessive beam current conditions before significant excessive radiation is developed.

SUMMARY OF THE INVENTION

The invention provides a method of limiting beam current magnitude of a charged particle beam within a particle accelerator system, including the steps of sensing continuously an electrical field magnitude associated with the charged particle beam, converting the electric field magnitude into a measure of the beam current magnitude of the charged particle beam, comparing a preset current level with the measure of beam current magnitude of the charged particle beam; and deactivating the charged particle beam whenever the measure of beam current magnitude exceeds the preset current level.

The invention also provides a beam current limiter for limiting maximum beam current in a charged particle accelerator. The beam current limiter includes a capacitive pickup electrode for capacitively interacting with the beam current to develop an alternating current signal indicative of the beam current magnitude. The beam current limiter further includes a signal processor for converting the alternating current signal to a variable direct current signal having a voltage dependent on the magnitude of the beam current magnitude. The beam current limiter further includes a threshold comparator for comparing the direct current signal to a predetermined reference voltage corresponding to a predetermined maximum beam current limit to develop an inhibit signal for inhibiting the beam current when the direct current signal exceeds the reference voltage.

It is an object of the present invention to provide a new and improved system for sensing and limiting beam current in a particle accelerator.

It is a further object of the present invention to provide a new and improved beam current limiter system that functions quickly to limit excessive beam current before significant excessive radiation is developed.

It is still another object of the present invention to provide a new and improved beam current limiter that senses directly the magnitude of the beam current.

It is still another object of the present invention to provide a new and improved beam current limiter that includes several levels of redundancy to ensure safety and reliability.

It is still another object of the present invention to provide a new and improved beam current limiter that tests itself and inhibits accelerator operation in the event the beam current limiter is not functioning properly.

BRIEF DESCRIPTION OF THE DRAWING

The features of the present invention which are believed to be novel are set forth with particularity in the appended claims. The invention, together with the further objects and advantages thereof, may best be understood by reference to the following description taken in conjunction with the accompanying drawings, wherein like reference numerals identify like elements, and wherein:

DESCRIPTION OF THE PREFERRED EMBODIMENT

Figure 1:
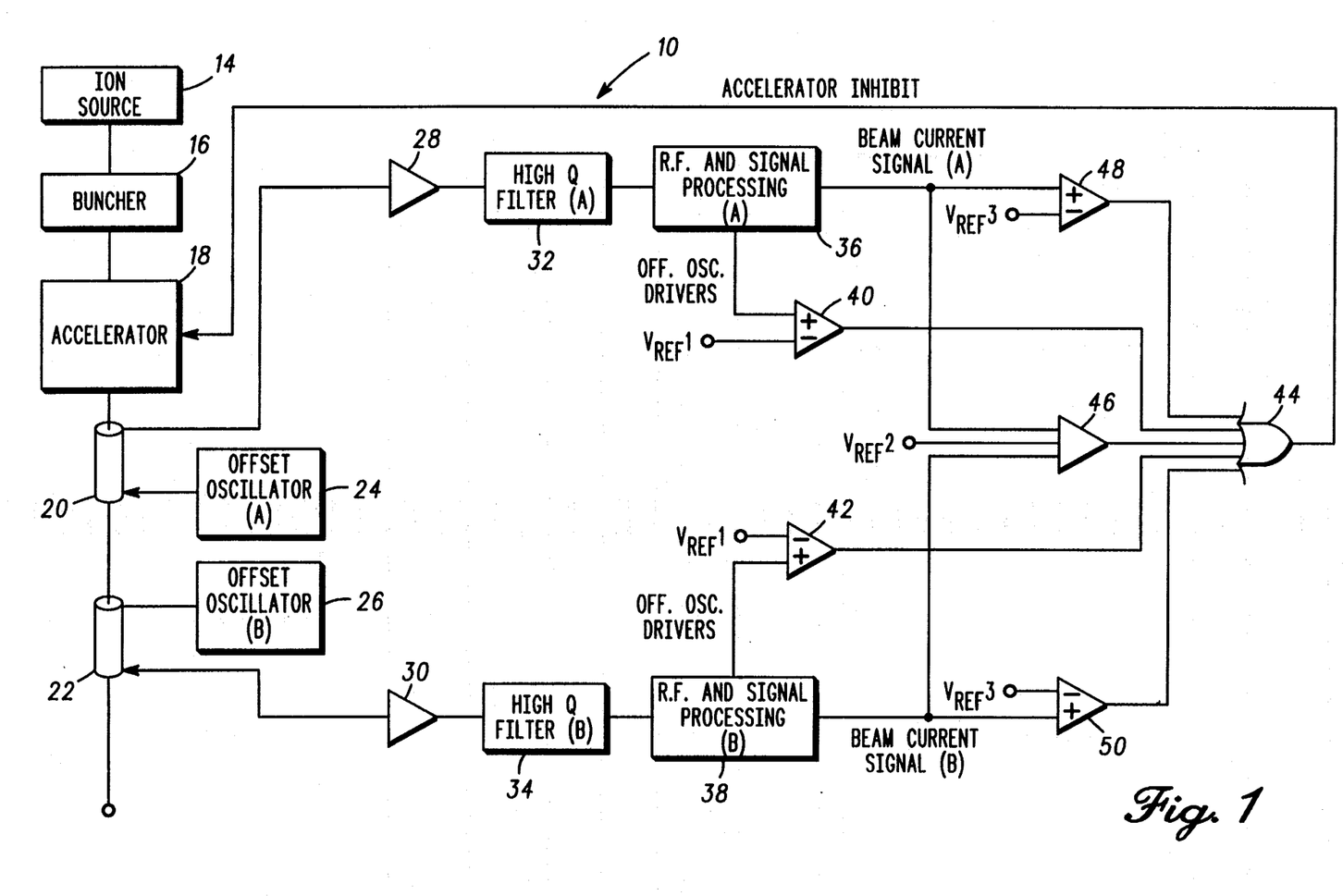
FIG. 1 is a simplified block diagram of a particle accelerator beam current limiter embodying various features of the invention.

Referring to the drawings, a particle accelerator 10 having a beam current limiter 12 embodying various features of the invention is shown in simplified block diagram form in FIG. 1. The particle accelerator 10 includes an ion source 14 of known construction that supplies electrically charged particles or ions to a particle buncher 16. In the illustrated embodiment, the ion source 14 provides heavy element ions, although it will be appreciated that other types of charged particles, such as electrons and protons, can be used. The buncher 16, in known manner, arranges the ions into a plurality of periodically timed bunches or packets at a predetermined cyclical rate or frequency. The bunched ions are then supplied to an accelerator 18 that, in known manner, accelerates the ions to the desired, pre-established energy level. The accelerated ions appear at the output of the accelerator 18 as a high energy current beam. The beam current magnitude is established by the number of ions entering the buncher 16 and, hence, is established by the ion source 14. The bunched nature of the ions is retained as the ions pass through the accelerator 18, and the period between bunches is maintained as the bunches pass through the accelerator 18. Accordingly, the cyclical rate or frequency ("beam frequency") at which the bunches appear at the output of the accelerator 18 is determined by the buncher 16.

As further illustrated in FIG. 1, the particle accelerator 10 is provided with a beam current limiter system 12 that continuously and directly monitors the magnitude of the beam current at the output of the accelerator 18 and automatically inhibits accelerator operation if the beam current exceeds a predetermined threshold. In addition, the beam current limiter 12 performs various internal self checks and inhibits accelerator operation in the event the beam current limiter 12 itself fails. The beam current limiter 12 exhibits a wide dynamic range and responds quickly to overcurrent conditions to inhibit accelerator operation within milliseconds of detecting an overcurrent condition. Accordingly, the beam current limiter 12 is well-suited for protecting against potentially harmful radiation that can result in the event the actual beam current at the output of the accelerator 18 exceeds that which is expected or desired.

In the illustrated embodiment, the beam current limiter 12 includes two independent channels, A and B, coupled, respectively, to independent capacitive pickup electrodes 20, 22. Each pickup electrode 20, 22 capacitively interacts with the beam current developed at the output of the accelerator 18 to develop a radio frequency (RF) voltage indicative of the beam current magnitude. The RF voltage thus developed includes components at the fundamental and harmonic frequencies of the beam current frequency.

An offset oscillator 24. 26 is associated with each of the capacitive pickup electrodes 20, 22. Each offset oscillator 24, 26 generates and applies to its associated electrode 20, 22 an RF signal ("offset oscillator signal") having a frequency displaced from the beam current frequency (or desired harmonic thereof) by a fixed, predetermined, offset amount. As will be discussed in greater detail below, the offset signals generated by the offset oscillators 24, 26 enhance system linearity, enable continuous monitoring of proper system operation and develop a low frequency difference or beat note (equal to the offset amount) that is easily processed by the beam current limiter circuitry.

The RF signals developed by the A channel and B channel pickup electrodes 20, 22 (together with the applied A channel and B channel offset oscillerator signals) are applied through respective A channel and B channel preamplifiers 28, 30 and high Q filters 32, 34 to respective A channel and B channel RF and signal processing circuits. The high Q filters 32, 34 provide a narrow system bandwidth to establish a low noise floor. This, in turn, improves the system noise figure to enhance the system dynamic range.

The A channel and B channel RF and signal processing circuits 36, 38 function generally to convert the amplified and filtered RF signals from each of the A channel and B channel electrodes 20, 22 into a respective variable DC voltage ("beam current signal") indicative of the beam current magnitude. The RF and signal processing circuits 36, 38 also provide an additional variable DC voltage ("offset oscillator drive level") indicative of the magnitude of the combined signal received from each pickup electrode 20, 22.

In accordance with one aspect of the invention, a plurality of independent, redundant checks or tests are performed on the A channel and B channel beam current signal voltages to verify proper system operation and to permit accelerator operation only within safe operating parameters. First, proper operation of the A channel and B channel pickup electrodes 20, 22, offset oscillators 24, 26, preamplifiers 28, 30, high Q filters 32, 34 and RF and signal processing circuits 36, 38 are verified by comparing the offset oscillator drive level signals developed by the A channel and B channel RF and signal processing circuits 36, 38 against a first fixed voltage reference $V_{ref}$ 1. The comparison is performed by means of a background level comparator 40, 42 in each channel.

For reasons that will be explained in greater detail below, the magnitude of the A channel and B channel offset oscillator signals are approximately four times greater than the expected magnitudes of the RF signals developed by the capacitive pickup electrodes 20, 22 in response to the maximum expected beam current. In the event the offset oscillator signals injected into the capacitive pickup electrodes 20, 22 for some reason do not ultimately reach the RF and signal processing circuits 36, 38, the resulting offset oscillator drive level voltage will be substantially less than expected. The reference voltage $V_{ref}$ 1 is selected so as to be higher than the drive level output that would result if only the beam current signal were applied to the RF and signal processing circuit 36, 38, but less than the drive level output voltage that would result when both the beam current signal and the offset oscillator signal both reach the RF and signal processing circuit 36, 38. Accordingly, the A channel and B channel background level comparators 40, 42 provide a first verification of proper system operation by ensuring that the drive level outputs of the the A channel and B channel RF and signal processing circuits 36, 38 each exceed the first reference voltage $V_{ref}$ 1.

A failure or malfunction in any of the offset oscillators 24, 26, preamplifiers 28, 30, high Q filters 32, 34 or any of the interconnections therebetween (and to the pickup electrodes 20, 22 and the RF and signal processing circuits 36, 38) will cause the offset oscillator drive level developed by the associated RF and signal processing circuit 36, 38 to be lower than expected. This, in turn, will cause the output of the associated background level comparator 40, 42 to go high. The outputs of the background level comparators 40, 42 are combined in a logic OR device 44 to generate the accelerator inhibit signal if the output of either background level comparator 40, 42 is high. So long as the accelerator inhibit signal is present, the accelerator 18 is prevented from operating.

A further internal verification of proper system function is provided by an additional or absolute value comparator 46 that senses the absolute difference in the variable DC output voltages of the A channel and B channel RF and signal processing circuits 36, 38, and then compares the resulting absolute value difference against a second reference voltage $V_{ref}$ 2. During normal system operation, it is expected that, because the same accelerated beam current passes through both the A channel and B channel pickup electrodes 20, 22, the resulting beam current signal voltages appearing at the outputs of the A channel and B channel RF and signal processing circuits 36, 38 will be substantially identical. Accordingly, the absolute difference between the A channel and B channel beam current signal voltages should be substantially zero and, hence, less than $V_{ref}$ 2.

In the event of a system failure or malfunction, or misadjustment or degradation in any upstream component or subsystem in either of the A or B channels, the absolute difference between the A and B voltages will become non-zero. The second reference voltage $V_{ref}$ 2 is set sufficiently high so as to be greater than the minor differences in the A channel and B channel voltages that result during normal system operation but less than the difference that would result in the event of a failure or malfunction in the A or B channels. In the event the absolute difference exceeds $V_{ref}$ 2, the output of the absolute value comparator 46 goes high thereby signaling the inhibit OR device 44 to generate the accelerator inhibit signal and thereby inhibit further accelerator operation.

Accelerator operation is also terminated or inhibited when the beam current magnitude exceeds a desired, predetermined limit. To this end, the beam current signals from the A channel and B channel RF and signal processing circuits are individually compared in respective maximum current comparators 48, 50 to a third reference voltage, $V_{ref}$ 3, corresponding to the maximum desired beam current. The A channel and B channel maximum current comparators 48, 50 independently compare the A channel and B channel beam current voltages against $V_{ref}$ 3 and provide logic high voltages at their outputs in the event the maximum desired beam current is exceeded. The outputs of the maximum current comparators 48, 50 are applied to respective inputs of the inhibit OR 44 device so that the accelerator inhibit signal is applied to the accelerator 18 in the event either maximum current comparator 48, 50 senses an overcurrent condition.

From the foregoing, it will be apparent that a logic high at the output of any of the comparators 40, 42, 46, 48 or 50 will generate the accelerator inhibit signal and thereby terminate or inhibit further accelerator operation. It will also be apparent that in the event of a failure in the beam current limiter system 12, accelerator operation will be inhibited unless substantially the same failure mode occurs in both the A and B channels at substantially the same time. To minimize the probability of such a common-mode failure, the A and B channels are preferably maintained as independent as possible and avoid sharing common power supplies, cabling and the like.

Figure 2:
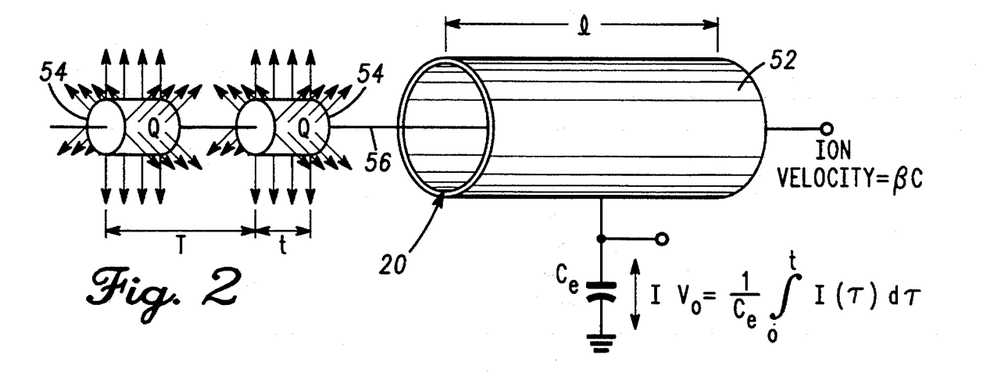
FIG. 2 is a diagrammatic view of one form of capacitive pickup electrode preferably used in the beam current limiter.

The construction and operation of the capacitive pickup electrodes 20, 22 can best be understood by reference to FIG. 2. Each capacitive pickup electrode 20, 22 comprises a conductive cylindrical segment or sleeve 52 of fixed length l having a hollow interior through which the beam current passes. As previously noted, the beam current itself comprises a plurality of ions arranged in regularly spaced bunches or packets 54. The ion bunches 54 move along the direction of the longitudinal axis 56 of the sleeve 52 interior with a velocity comprising some fraction, $\beta$, of the speed of light. Each ion bunch has associated with it a charge Q, and the period between adjacent bunches is the time T. The time required for each bunch 54 to pass a fixed point in space is a function of the space distribution of the ions and the ion velocity $\beta$, and, in FIG. 2, is designated t.

As further illustrated in FIG. 2, a radially outwardly directed electric field is associated with each of the charge bunches 54. As each charge bunch 54 passes through the sleeve, the voltage of the sleeve referenced to ground varies according to the equation $$V_o = \frac{1}{C_e} \int_r^t I(\tau)d\tau$$

where $C_e$ is the equivalent capacitance of the sleeve 52 and $I(\tau)$ is the equivalent instantaneous beam current represented by the charge passing through the sleeve.

It will be appreciated that so long as the time $T_d$ required for an ion bunch 54 to drift through the cylindrical sleeve $$\left(\text{i.e., } T_d = \frac{l}{\beta c}\right)$$

is greater than or equal to the time width t of the bunch 54, then the integral shown above represents simply the total charge Q per bunch, and the output voltage of the electrode will be $$V_o = \frac{Q}{C_e}.$$

Accordingly, for such a condition, the average beam current is given by the equation $I = V_o C_e F$ where I represents the average beam current, $V_o$ represents the peak value of electrode voltage, $C_e$ represents the electrode capacitance and F represents the bunch repetition rate 1/T. Accordingly, it is possible to determine the average beam current by sensing the peak electrode voltage. This, however, would require such a wide system bandwidth as to limit the system dynamic range.

To permit the determination of the average beam current while maintaining a narrow system bandwidth, the beam current limiter is preferably operated so as to respond to a harmonic of the bunch repetition frequency F. In the case of a linear accelerator 18 used in scientific research and operated at a bunch repetition frequency of 12.125 MHz, the second harmonic (i.e., 24.250 MHz) is preferably selected. In such a linear accelerator, the presence of 48 MHz and 72 MHz resonators results in a 24 MHz frequency component in the accelerated beam even if a non-bunched or DC beam is delivered to the input of the linear accelerator 18. Accordingly, use of the second harmonic enables the beam current limiter to sense the accelerated beam current even with a DC or non-bunched beam input that can result from the failure of the buncher 16.

Furthermore, Fourier transform theory shows that, when the second harmonic is used, the second harmonic amplitude increases as a function of decreasing ion velocity. Thus, lower velocity ions will result in somewhat inflated current readings. However, over the limited velocity range of particular linear accelerators (e.g., 4.5% to 6.5% c) the effect is not of practical consequence if the maximum current threshold is set on the basis of the highest velocity ions encountered by the pickup electrodes 20, 22. Lower velocity ions will simply result in a trip or perceived overcurrent condition at progressively smaller beams currents. Safety is not compromised because the desired maximum beam current is never actually exceeded.

To provide operation at the second harmonic of the beam frequency, each of the offset oscillators 24, 26 operates at approximately the second harmonic frequency, and the high Q filters 32, 34 are tuned to the second harmonic frequency. The actual offset oscillator frequencies are offset from the actual second harmonic frequency by a desired offset or beat note frequency. In the illustrated embodiment, which operates at a second harmonic frequency of 24.250 MHz, a 2.5 KHz beat note was utilized and each offset oscillator operated at 24.2525 MHz.

Figure 3:
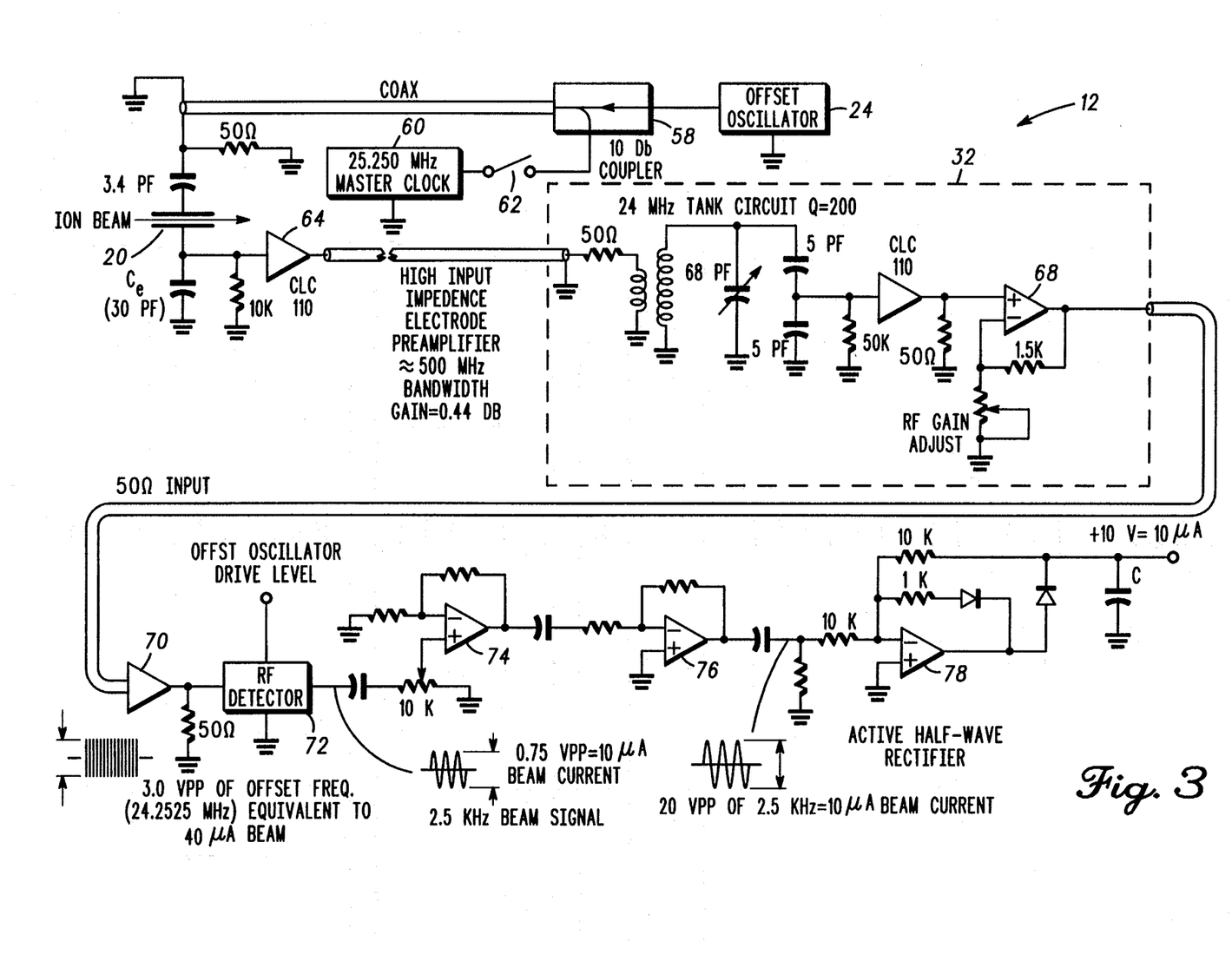
FIG. 3 is a simplified schematic diagram of one beam sensing channel of beam current limiter embodying various features of the invention.

One channel of an actual beam current limiter 12 embodying various features of the invention is illustrated in the simplified schematic diagram of FIG. 3. The beam current limiter 12 operates at the second harmonic of a 12.125 MHz linear accelerator and, hence, is configured for 24 MHz operation. The offset oscillator 24 is adjusted to operate at 24.2525 MHz and its output is applied through a 10 dB coupler 58 to the capacitive pickup electrode 20. A 24.250 MHz master clock oscillator 60 is also provided and is used as a beam simulator for testing and calibrating the beam current limiter 12. The output of the master clock oscillator 60 can be selectively applied to the pickup electrode 20 through a switch 62 and the 10 dB coupler 58 to simulate the passage of an ion beam through the electrode 20.

The combined offset oscillator and RF beam current magnitude signals from the electrode 20 are coupled through a high impedance, wideband buffer amplifier 64 to a nominal 24 MHz tank circuit 66 having a Q of approximately 200. The tank circuit 66 is tuned to a center frequency of 24.25125 MHz and provides a 3 db bandwidth of approximately 121 KHz. The output of the tank circuit 66 is coupled through a variable gain RF amplifier 68 and an additional amplifier 70 to an RF detector 72. The RF detector 72 rectifies and filters the amplified pickup electrode signal to develop a variable DC voltage whose magnitude depends primarily on the magnitude of the offset oscillator signal component reaching the detector 72. This DC signal comprises the offset oscillator drive level signal and is provided to the background level comparator 40 (FIG. 1) to verify the presence of the offset oscillator signal and proper functioning of the intervening subsystems. In addition, the RF detector 72 extracts the 2.5 KHz difference signal or beat note from the pickup electrode signal and supplies the 2.5 KHz signal through two stages of amplification 74, 76 to an active halfwave rectifier 78. The active halfwave rectifier 78, in turn, converts the 2.5 KHz beam signal to an equivalent variable DC voltage.

In the particular system illustrated, the accelerator beam currents are expected to range between a minimum of 10 nanoamperes and a maximum of 10 microamperes. The variable DC beam current signal voltage at the output of the active halfwave rectifier is expected to vary linearly between 0 volts (in the absence of bunched beam) and 10 volts (when bunched beam current is 10 microamperes). The magnitude of the offset oscillator signal is set so that, when it combines with the second harmonic beam current magnitude signal sensed by the pickup electrode 20, the offset oscillator signal is amplitude modulated by the beam magnitude signal to a maximum of 25% modulation at the maximum beam current, i.e., 10 microamperes. By limiting modulation to 25% or less, distortion effects become negligible and a clean 2.5 KHz sine wave results when the signal is ultimately demodulated.

Figure 4A:
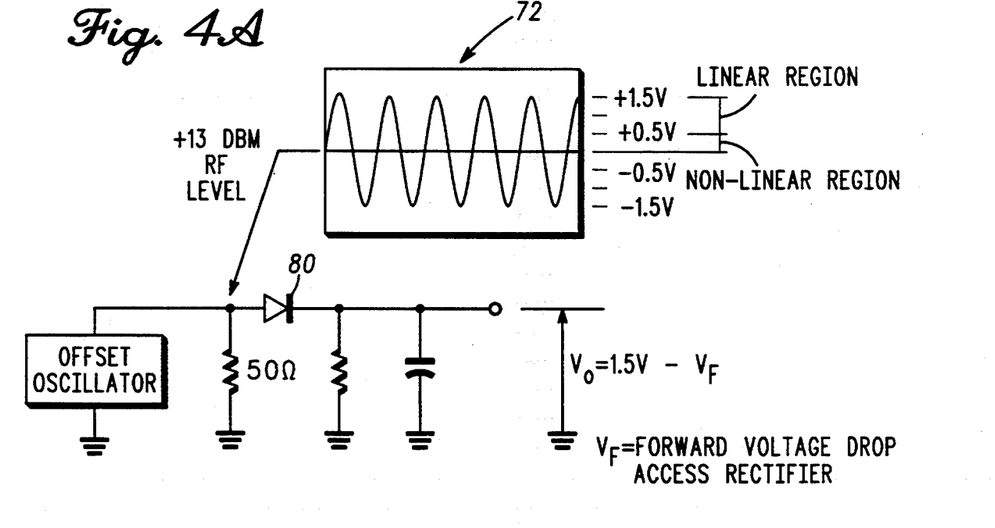
FIGS. 4a and 4b are, respectively, (a) a schematic diagram of a diode detector used in one preferred form of beam current limiter, and (b) a waveform diagram showing a preferred 25% (maximum) amplitude modulation of an applied offset oscillator signal, useful in understanding how the offset oscillator signal provides operation of a diode detector in a linear operating region.
Figure 4B:
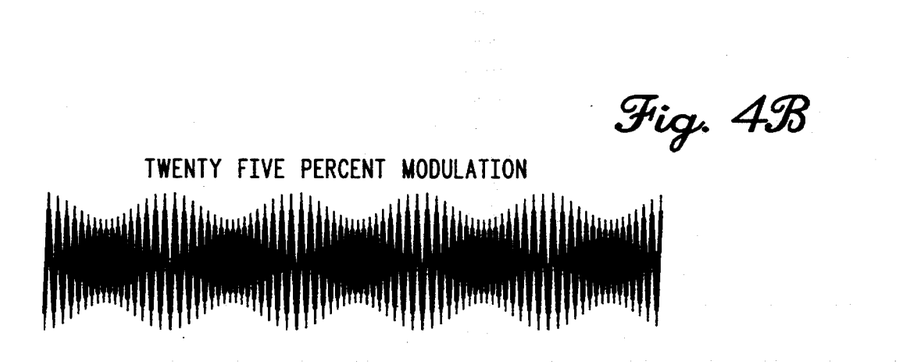

As shown in FIGS. 4a and 4b, the combined gain of the various amplifier stages is preferably selected so that at the maximum modulation (i.e., 25%), the modulation envelope of the signal remains fully within the linear region of the RF detector diode 80. By operating at all times within the linear region of the detector diode 80, linearity between the magnitude of the beat note and the magnitude of the sensed beam current is maintained.

Figure 5:
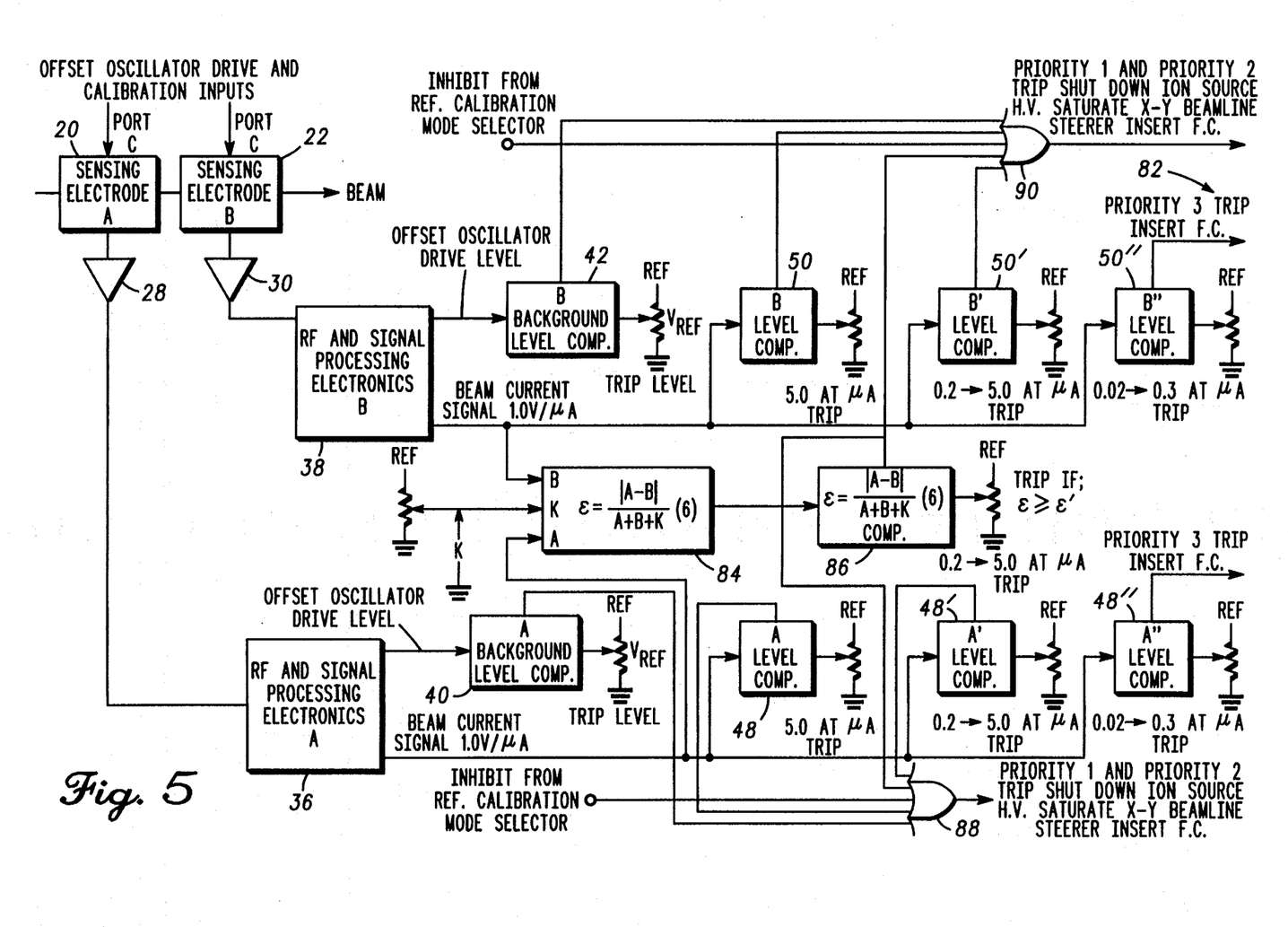
FIG. 5 is a block diagram of one preferred beam current limiter that is responsive to three discrete trip current levels.

A system block diagram of one preferred beam current limiter 82 is shown in FIG. 5. In this system, the offset oscillator drive level signal in each channel is compared (40, 42) to a trip level reference to verify the presence of the offset oscillator signal. If the offset oscillator signal is not present in either channel, an inhibit signal is developed to shut down the accelerator 18. The variable DC beam current signals of both channels are also compared to ensure they are substantially similar. First, at 84, normalized channels error voltage $\epsilon$ is developed according to the expression:

$$\epsilon = \frac{A/B}{A + B + K}(G)$$

where A is the DC beam current voltage of channel A, B is the DC beam current voltage of channel B, K is a denominator offset constant determined by a preselected reference voltage, and G is a gain function. Next, the quantity $\epsilon$ thus determined is compared 86 to a preselected reference $\epsilon'$. If $\epsilon$ equals or exceeds $\epsilon'$ thus indicating disagreement between the A channel and B channel beam current signals, an inhibit signal is developed to shut down the accelerator 18.

In addition to these trip conditions (which essentially result from failure or malfunction within the beam current limiter system itself), the beam current limiter 82 also compares the magnitude of the beam current signal in each channel against three separate thresholds representing three difference accelerator beam current levels. This is accomplished by three separate voltage or level comparators 48, 48', 48" and 50, 50', 50" in each channel. The level comparators 48-50" develop inhibit signals of three different priorities depending on the seriousness and magnitude of the sensed overcurrent condition.

The first trip limit is set at a relatively high, fixed beam current limit that should never be exceeded (e.g., 5.0 microamperes). As noted, this trip limit is fixed, cannot ordinarily be changed by the accelerator operating personnnel and is dictated primarily by the capabilities of the particular accelerator. Beam currents in excess of this maximum or first trip limit current result in a highest priority or "priority 1" trip event.

The second trip level is under the control of the accelerator operators and can be set less than or equal to the fixed trip limit (e.g., 0.2 to 5.0 microamperes). Sensed beam currents in excess of the second trip limit result in a "priority 2" trip event.

The third trip limit is also set by the operating personnel and typically is set substantially lower than the second trip limit (e.g., 0.0 to 0.3 microamperes). Beam currents in excess of the third trip limit give rise to a "priority 3" trip event.

The purpose of the first trip limit is to ensure that the maximum safe operating capabilities of the accelerator 18 are never exceeded. In the event of a priority 1 trip event, the ion source 14 is shut down, the x-plane and y-plane beam steerers of the particle accelerator 18 are saturated to divert the beam away from the centerline of the accelerator, and a Faraday cup (not shown) is inserted into the beam. The effect is to interrupt the accelerated beam as quickly and effectively as possible.

The second trip limit is intended to avoid conditions wherein the beam current magnitude, while still within the maximum capability of the accelerator, nevertheless exceeds a level that is neither necessary for the particular application or experiment being conducted or that could cause harm to the operating personnel. A priority 2 trip event has the same effect as a priority 1 event, i.e., the ion source is shut down, the ion beam is deflected and a Faraday cup is inserted.

The third trip limit is set substantially at the maximum beam current expected or desired in any particular application. Accordingly, the third trip level is typically substantially less than either the maximum current capacity of the accelerator or a lesser current level that could still be hazardous. In the event of a priority 3 trip event, the Faraday cup is inserted into the beam, but the ion source is not shut down and the ion beam is not deflected.

Because any failure or malfunction in the beam current limiter itself could result in excessive beam currents, the ion source is shut down, the beam is deflected and the Faraday cup is inserted whenever a discrepancy is noted in the offset oscillator signal background level in either channel, or if there is disagreement between the A channel and B channel beam current signals. Accordingly, in each channel, the outputs of the background level comparators 40, 42, the absolute value comparators 86, and the first and second trip limit comparators 48-50" are combined in a logic OR function 88, 90 to develop an appropriate control signal in the event of any such occurrence in either channel. The priority 3 trip event that occurs when the detected beam current exceeds only the lowest current limit does not require such drastic action and, accordingly, the third current limit comparators 48", 50" apply an appropriate control signal only to the Faraday cup.

The beam current limiter herein shown and described is effective in terminating excess beam current events with high reliability and within very short periods. In contrast to indirect monitoring systems that rely on appropriately located radiation detectors, the beam current limiter herein shown and described directly measures the actual beam current magnitude at the output of the accelerator. The possibility of failing to sense an actual overcurrent condition is thus greatly minimized. The use of two, separate, electrically and physically independent sensing channels provides redundancy and permits the system to contiuously compare the two channels to detect automatically a failure or malfunction in either channel. This minimizes the possibility of operating the accelerator when the operability and reliability of the beam current limiter is compromised. Operation of the system at the second harmonic of the beam current frequency further enhances reliability and effectiveness by enabling the system to detect accelerated beam currents even in the event a buncher fails and a DC ion stream is provided to the accelerator. Injection of the offset oscillator signals in conjunction with limited maximum amplitude modulation thereof improves system linearity by reducing distortion and ensuring that RF detector diodes operate at all times in a linear region. Operation at the second harmonic of the beam current frequency further permits use of a narrow system bandwidth to improve the system noise figure and thereby enhance the system dynamic range. The use of multiple, fixed and controllable trip current limits further enhances safety and reliability by providing additional redundancy and further enhances the overall effectiveness of the beam current limiter by enabling the operating personnel to tailor certain trip current limits to the requirements of a particular application or experiment.

Although the beam current limiter has been shown and described in the context of a 12.125 MHz heavy ion accelerator used in scientific research applications, it will apparent to those skilled in the art that the system and principles described herein can be readily adapted to other applications. For example, the system can be used in connection with accelerators employing charged particles, such as electrons and protons, other than heavy ions. Furthermore, the system can be readily adapted to medical applications, such as radiation treatment, wherein it is imperative to avoid excessive radiation doses.

In such radiation treatments it is generally desired to achieve a 38 cm. characteristic penetration depth in the patient. The most preferred treatments are performed using particles which also have a well defined energy deposition peak range which allows precise deposition of the radiation therapy to a particular minor geometry. Electron beams are typically of 6-20 MeV energy, proton beams are about 250 MeV energy and neon ions have an energy of about 12 GeV to achieve the desired controlled stopping range. Charged particle beams can also be used to generate gamma rays and other high energy non-charged secondary radiation for both patient radiation treatment and for scientific research. For such uses the invention can be used to control the secondary rediation levels as well, without need to resort to prior art external radiation monitors of the secondary radiation.

Although specific frequencies, voltages, gains and circuit configurations have been disclosed, it will be apparent to those skilled in the art that modifications can be made to suit particular applications and the description provided herein is intended to be illustrative rather than limiting.

While preferred embodiments have been illustrated and described, it should be understood that changes and modifications can be made therein without departing from the invention in its broader aspects. Various features of the invention are defined in the following claims.

What is claimed is:

1. A method of limiting beam current of a charged particle beam within a particle accelerator system, comprising the steps of:
    (a) sensing continuously an electrical field magnitude associated with the charged particle beam, said sensing of the electric field magnitude performed without directly measuring the charge particle beam current;
    (b) converting the electric field magnitude into a measure of the beam current magnitude of the charged particle beam;
    (c) comparing a preset current level with the measure of beam current magnitude of the charged particle beam; and
    (d) deactivating the charged particle beam whenever the measure of beam current magnitude exceeds the preset current level.

2. The method as defined in claim 1 wherein the step of sensing the electrical field magnitude comprises using a capacitive pickup electrode as part of the particle accelerator system.

3. The method as defined in claim 2 further including an offset RF oscillator electrically coupled to the capacitive pickup electrode with the offset RF oscillator generating an RF signal different from a pulse frequency of the charged particle beam thereby enabling converting the electrode field magnitude into the measure of the beam current magnitude.

4. The method as defined in claim 1 wherein the step of converting the electrode field magnitude comprises applying to the charged particle beam electric field magnitude an offset RF signal having a frequency displaced from the frequency of a pulsed form of the charged particle beam.

5. The method as defined in claim 4 wherein the step of applying of the offset RF signal generates a low frequency RF signal characteristic of the beam current magnitude.

6. The method as defined in claim 5 wherein a signal processing circuit converts the low frequency RF signal into a DC voltage characteristic of the beam current magnitude.

7. The method as defined in claim 6 wherein at least one independent test is performed periodically involving the DC voltage.

8. The method as defined in claim 7 wherein the independent test includes at least one of monitoring proper operation of (a) a capacitive pickup electrode for sensing the electric field magnitude, (b) the offset RF oscillator, (c) preamplifiers coupled to the signal processing circuit and (d) high Q filters coupled to the signal processing circuit.

9. The method as defined in claim 8 wherein the step of monitoring proper operation comprising comparing offset oscillator drive level signals developed by the signal processing circuit to a first fixed voltage reference.

10. The method as defined in claim 1 wherein at least two independent channels are used to perform steps (a)-(c) allowing further verification of proper system function by comparing the difference in measure of beam current magnitude from each independent channel to a second fixed voltage reference.

11. A beam current limiter for limiting maximum beam current in a charged particle accelerator, said beam current limiter comprising:
    a capacitive pickup electrode for capacitively interacting with the beam current to develop an alternating current signal indicative of the beam current magnitude without said capacitive pickup electrode directly measuring the beam current from the accelerator;
    signal processing means for converting said alternating current signal to a variable direct current signal having a voltage dependent on the magnitude of the beam current magnitude; and
    threshold comparator means for comparing said direct current signal to a predetermined reference voltage corresponding to a predetermined maximum beam current limit to develop an inhibit signal for inhibiting the beam current when said direct current signal exceeds said reference voltage.

12. A beam current limiter as defined in claim 11 wherein said capacitive pickup electrode comprises a conductive sleeve having a hollow interior through which beam current can pass.

13. A beam current limiter as defined in claim 11 wherein the voltage of said variable direct current signal is substantially proportional to the magnitude of the beam current.

14. A beam current limiter system for limiting beam current magnitude in a bunched charged particle accelerator so that the beam current is inhibited if the beam current exceeds a predetermined limit, said beam current limiter comprising:
    first and second capacitive pickup electrodes for independently developing separate alternating current beam magnitude signals indicative of the beam current sensed by each said electrode;
    first and second offset oscillators for developing and injecting into each of said first and second pickup electrodes, respectively, an alternating current offset signal having a frequency displaced, by a predetermined amount, from the bunching frequency of the accelerator or some preselected harmonic thereof;
    first and second signal processing means associated, respectively, with said first and second pickup electrodes and said first and second offset oscillators and responsive to said alternating current beam magnitude signals and said alternating current offset signals for producing, with respect to each of said first and second electrodes, a first variable direct current signal indicative of the magnitude of said offset signal and a second variable direct current signal indicative of the beam current magnitude sensed by the respective ones of said first and second electrodes;
    first comparators means for comparing the first variable direct current signals generated by said first and second signal processing means to a known reference to develop an inhibiting signal if the first variable direct current signal developed by either said first or second signal processing means does not exceed said first reference;

second comparator means for comparing said second variable DC signals of said first and second signal processing means against each other to develop an inhibit signal if the absolute difference between said second variable DC signals of said first and second signal processing means exceeds a second predetermined threshold; and third comparator means for independently comparing said second variable DC signals of said first and second signal processing means against a third predetermined threshold to develop an inhibit signal if the second variable DC signal of either said first or second signal processing means exceeds said third pre-established threshold.

15. A beam current limiter as defined in claim 14 wherein said alternating current beam magnitude signal amplitude modulate said alternating current offset signal and wherein said beam current limiter further includes means for limiting said amplitude modulation to substantially 25% or less.

16. A beam current limiter as defined in claim 15 wherein said first and second signal processing means each include a diode detector and the magnitude of said offset signal is sufficient to maintain the modulation envelope of said amplitude modulated offset signal within the linear operating region of said diode detector.

17. A beam current limiter as defined in claim 14 further comprising a narrow bandwidth high Q filter associated with each of said first and second pickup electrodes for limiting the bandwidth of said beam current limiter system.

18. A beam current limiter system as defined in claim 14 further comprising additional comparators means for comparing said second variable direct current signals generating by said first and second signal processing means against additional predetermined references to develop inhibit signals at additional beam current thresholds.

* * * * *

UNITED STATES PATENT AND TRADEMARK OFFICE
CERTIFICATE OF CORRECTION

PATENT NO. : 5,440,210
DATED : August 8, 1995
INVENTOR(S) : Bogaty et al.

It is certified that error appears in the above-identified patent and that said Letters Patent is hereby corrected as shown below:

Col 8, Line 51, omit "A/B" and insert — A-B —;

Col. 10, Line 57, omit "minor" and insert — tumor—.

Signed and Sealed this

Eighth Day of October, 1996

Attest:

BRUCE LEHMAN

Attesting Officer

Commissioner of Patents and Trademarks